(12) United States Patent
Cao et al.

(10) Patent No.: US 11,549,804 B2
(45) Date of Patent: Jan. 10, 2023

(54) DETECTION APPARATUS AND METHOD FOR FLOW DEFORMATION OF FOUNDATION LAYER IN HORIZONTAL DIRECTION

(71) Applicants: Sun Yat-sen University, Guangzhou (CN); Southern Marine Science and Engineering Guangdong Laboratory (Zhuhai), Zhuhai (CN)

(72) Inventors: Dingfeng Cao, Guangzhou (CN); Chengchao Guo, Guangzhou (CN); Pengpeng Ni, Guangzhou (CN); Fuming Wang, Guangzhou (CN)

(73) Assignees: Sun Yat-sen University; Southern Marine Science and Engineering Guangdong Laboratory (Zhuhai)

( * ) Notice: Subject to any disclaimer, the term of this patent is extended or adjusted under 35 U.S.C. 154(b) by 111 days.

(21) Appl. No.: 17/337,190

(22) Filed: Jun. 2, 2021

(65) Prior Publication Data
US 2022/0228853 A1 Jul. 21, 2022

(30) Foreign Application Priority Data
Jan. 15, 2021 (CN) .......................... 202110054185.4

(51) Int. Cl.
*G01N 33/24* (2006.01)
*G01B 11/16* (2006.01)
(Continued)

(52) U.S. Cl.
CPC ............... *G01B 11/16* (2013.01); *E02D 1/02* (2013.01); *E02D 1/08* (2013.01); *E02D 33/00* (2013.01); *G01L 1/242* (2013.01); *G01N 33/24* (2013.01)

(58) Field of Classification Search
CPC .. E02D 1/00; E02D 1/02; E02D 1/022; E02D 1/027; E02D 1/08; E02D 33/00; G01L 1/242; G01B 11/18; G01B 11/20
See application file for complete search history.

(56) References Cited

U.S. PATENT DOCUMENTS

2007/0069115 A1* 3/2007 Huang ................... G01B 11/18
250/227.14
2017/0328743 A1* 11/2017 Yamazaki ............... G01L 1/242
(Continued)

FOREIGN PATENT DOCUMENTS

CN 102345796 A 2/2012
CN 202869443 U * 4/2013
(Continued)

OTHER PUBLICATIONS

English translation of CN 112648931 A.*
(Continued)

*Primary Examiner* — Herbert K Roberts
(74) *Attorney, Agent, or Firm* — Haynes and Boone, LLP (57) ABSTRACT

Disclosed is detection apparatus for flow deformation of foundation layer in horizontal direction including: housing, rotation assembly rotatably disposed within accommodation cavity of the housing, and measurement assembly including first optical fiber lead wire, first optical fiber sensor disposed on first optical fiber lead wire, second optical fiber lead wire, and second optical fiber sensor disposed on second optical fiber lead wire, and disposed within the accommodation cavity. First optical fiber sensor is configured to measure tensile strain of first optical fiber lead wire and first optical fiber sensor before and after the rotation assembly rotates; second optical fiber sensor is configured to measure tensile strain of second optical fiber lead wire and second optical fiber sensor before and after the rotation assembly rotates, to obtain strain amount and displacement change amount, and (Continued)

further to obtain flow deformation degree and flow deformation direction of soil mass of the foundation layer.

10 Claims, 3 Drawing Sheets

(51) Int. Cl.
    *E02D 1/02*         (2006.01)
    *E02D 1/08*         (2006.01)
    *E02D 33/00*       (2006.01)
    *G01L 1/24*         (2006.01)

(56) References Cited

U.S. PATENT DOCUMENTS

| | | | | |
|---|---|---|---|---|
| 2019/0338487 A1* | 11/2019 | Niezrecki | ............ | E02D 27/425 |
| 2020/0124416 A1* | 4/2020 | Mancini | ............ | G01C 9/00 |
| 2021/0270685 A1* | 9/2021 | Hong | ............ | G01L 1/242 |

FOREIGN PATENT DOCUMENTS

| | | | | | |
|---|---|---|---|---|---|
| CN | 103543287 | A | | 1/2014 | |
| CN | 108037312 | A | | 5/2018 | |
| CN | 108169514 | A | * | 6/2018 | ............ G01P 13/02 |
| CN | 108169514 | A | | 6/2018 | |
| CN | 207675786 | U | * | 7/2018 | ............ G01P 13/02 |
| CN | 108693379 | A | | 10/2018 | |
| CN | 110440696 | A | * | 11/2019 | ............ G01B 11/02 |
| CN | 111637844 | A | * | 9/2020 | ............ G01B 11/18 |
| CN | 111637844 | A | | 9/2020 | |
| CN | 112066945 | A | * | 12/2020 | |
| CN | 212253997 | U | * | 12/2020 | ............ G01B 11/18 |
| CN | 212253997 | U | | 12/2020 | |
| CN | 112648931 | A | * | 4/2021 | ............ E02D 17/02 |
| JP | 2001153879 | A | | 6/2001 | |
| JP | 2001227919 | A | * | 8/2001 | |
| JP | 2002048675 | A | * | 2/2002 | |
| KR | 20080110293 | A | * | 12/2008 | |
| KR | 20100032286 | A | * | 3/2010 | |
| KR | 20120104679 | A | * | 9/2012 | |
| KR | 20150009270 | A | * | 1/2015 | |
| KR | 20150025853 | A | * | 3/2015 | |
| WO | WO-2019093966 | A1 | * | 5/2019 | ............ E02D 1/022 |

OTHER PUBLICATIONS

English translation of CN 212253997 U.*
English translation of CN 112066945 A.*
English translation of CN 111637844 A.*
English translation of CN 110440696 A.*
English translation of CN 207675786 U.*
English translation of CN 108169514 A.*
English translation of KR 20150025853 A.*
English translation of KR 20150009270 A.*
English translation of CN 202869443 U.*
English translation of KR 20120104679 A.*
English translation of KR 20100032286 A.*
English translation of KR 20080110293 A.*
English translation of JP 2002048675 A.*
English translation of JP 2001227919 A.*
Office Action dated Sep. 28, 2021 issued in related Chinese patent application No. 202110054185.4 (19 pages).

* cited by examiner

DETECTION APPARATUS AND METHOD FOR FLOW DEFORMATION OF FOUNDATION LAYER IN HORIZONTAL DIRECTION

CROSS-REFERENCE TO RELATED APPLICATION(S)

This application claims priority to Chinese Patent Application No. 202110054185.4, filed Jan. 15, 2021, the disclosure of which is incorporated herein by reference in its entirety.

TECHNICAL FIELD

The present disclosure relates to the technical field of soil mass measurements, and in particular to a detection apparatus and a detection method for flow deformation of a foundation layer in a horizontal direction.

BACKGROUND

One of the causes of damage to buildings lies in the settlement of foundation, which is caused by many reasons such as underground dewatering, drainage consolidation, and compaction and creep deformation under load effects. According to different directions, deformation of a soil mass is divided into a settlement deformation component in the vertical direction and a flow deformation component in the horizontal direction. The settlement deformation in the vertical direction commonly exists in various soil mass, while the flow deformation in the horizontal direction commonly exists in a foundation layer with high water content, low strength and rich clay particles.

A conventional method for determining the deformation of foundation in the vertical direction is to adopt a level gauge to measure the surface elevation so as to determine the settlement amount of foundation. However, this method has a high labor cost and cannot be implemented in continuous testing. In order to make up for the defects of manual leveling, the technology of interferometric synthetic aperture radar (InSAR) has been adopted in recent years, which can be used for testing of deformation for an earth surface of a whole site or area in the vertical direction. However, through the above manner, only the settlement amount of the earth surface can be obtained, and the deformation distribution for the profile of the foundation layer cannot be obtained. The foundation layer which mainly deforms as well as the deformation form cannot be determined.

In order to accurately obtain the deformation profile of the foundation layer, a tester implants distributed optical fiber sensors through drilling a hole, for measurement. However, through this manner, only the settlement deformation of the foundation layer in the vertical direction can be measured, but the flow deformation in the horizontal direction cannot be tested, and thus the flow deformation direction in the horizontal direction cannot be determined.

SUMMARY

An object of the present disclosure is to provide a detection apparatus for flow deformation of a foundation layer in the horizontal direction, so that the flow deformation of a foundation layer in the horizontal direction is tested, and thus the deformation condition and the flow deformation direction of the foundation layer in the horizontal direction are obtained.

As conceived above, the technical schemes adopted in the present disclosure are as follows.

A detection apparatus for flow deformation of a foundation layer in a horizontal direction, includes: a housing, a rotation assembly and a measurement assembly. An accommodation cavity is provided inside the housing, and a top end of the housing is provided with an upper opening, communicating with the accommodation cavity. The rotation assembly includes a blade and is rotatably disposed within the accommodation cavity, a top end of the rotation assembly plugs the upper opening, and in response to a flow deformation of a foundation layer to be detected, a flowing soil mass is able to push the blade to rotate so that the rotation assembly rotates relative to the housing around an axis of the rotation assembly. The measurement assembly is disposed within the accommodation cavity, and the measurement assembly includes an optical fiber sensor and an optical fiber lead wire. The optical fiber sensor includes a first optical fiber sensor and a second optical fiber sensor. The optical fiber lead wire includes a first optical fiber lead wire and a second optical fiber lead wire. The first optical fiber lead wire is provided with the first optical fiber sensor, one end of the first optical fiber lead wire is fixed to a first positioning point of the rotation assembly, the other end of the first optical fiber lead wire is fixed to a second positioning point of the housing, and the first optical fiber sensor is configured to: measure an initial value of tensile strain of the first optical fiber lead wire and the first optical fiber sensor before the rotation assembly rotates, and measure a final value of tensile strain of the first optical fiber lead wire and the first optical fiber sensor after the rotation assembly rotates. The second optical fiber lead wire is provided with the second optical fiber sensor, one end of the second optical fiber lead wire is fixed to a third positioning point of the rotation assembly, the other end of the second optical fiber lead wire is fixed to a fourth positioning point of the housing, and the second optical fiber sensor is configured to: measure an initial value of tensile strain of the second optical fiber lead wire and the second optical fiber sensor before the rotation assembly rotates, and measure a final value of tensile strain of the second optical fiber lead wire and the second optical fiber sensor after the rotation assembly rotates. The first positioning point and the third positioning point are located on a same side of the rotation assembly, the second optical fiber lead wire and the first optical fiber lead wire are arranged at an obtuse angle, and the first optical fiber lead wire and/or the second optical fiber lead wire penetrate out of the housing to be connected to a receiving apparatus.

In some implementations, this apparatus further includes an elastic piece, and a bottom end of the rotation assembly is connected to a bottom of the housing through the elastic piece.

In some implementations, the rotation assembly further includes an upper end cover and a rotating shaft, the upper end cover is connected to the rotating shaft and plugs the upper opening, and the upper end cover is provided with the blade in an extending radial direction.

In some implementations, the rotating shaft includes an upper diameter end and a lower diameter end, the accommodation cavity is divided into an upper chamber and a lower chamber being communicated with the upper chamber, the upper diameter end is accommodated in the upper chamber, and the upper diameter end and an inner wall of the upper chamber define an annular space, the measurement assembly is located within the annular space, the lower diameter end is accommodated in the lower chamber, and balls are filled between the lower diameter end and an inner wall of the lower chamber.

In some implementations, a bottom of the lower diameter end is provided with a baffle, and the baffle is configured to block the balls.

In some implementations, the upper end cover is provided with a wire hole, and the first optical fiber lead wire and/or the second optical fiber lead wire are penetrated out through the wire hole.

In some implementations, the upper end cover is connected to the rotating shaft through a screw.

In some implementations, a bottom end of the housing is provided with a lower opening, the lower opening is communicated with the accommodation cavity, the housing further includes a bottom end cover, and the bottom end cover plugs the lower opening.

In some implementations, this apparatus further includes a connecting rod, where a central hole is provided on both the rotation assembly and the housing simultaneously along the axis of the rotation assembly and the housing, and the connecting rod is disposed to pass through the central hole.

Another object of the present disclosure is to provide a detection method for flow deformation of a foundation layer in a horizontal direction, so that a flow deformation degree and a flow deformation direction of a soil mass in the horizontal direction are monitored.

As conceived above, the technical schemes adopted in the present disclosure are as follows.

A detection method for flow deformation of a foundation layer in a horizontal direction, adopts the detection apparatus for flow deformation of a foundation layer in a horizontal direction described above and includes steps described below.

Step S0, a foundation layer is drilled, and the detection apparatus for flow deformation of a foundation layer in a horizontal direction is disposed inside the foundation layer;

Step S1, before the rotation assembly rotates, the first optical fiber sensor measures an initial value of tensile strain of the first optical fiber lead wire and the first optical fiber sensor; and the second optical fiber sensor measures an initial value of tensile strain of the second optical fiber lead wire and the second optical fiber sensor;

Step S2, a soil mass flows to push the blade to rotate, and after the rotation assembly rotates, the first optical fiber sensor measures a final value of tensile strain of the first optical fiber lead wire and the first optical fiber sensor to obtain a first strain amount and a first displacement change amount; and after the rotation assembly rotates, the second optical fiber sensor measures a final value of tensile strain of the second optical fiber lead wire and the second optical fiber sensor to obtain a second strain amount and a second displacement change amount; and Step S3, the first optical fiber sensor and the second optical fiber sensor transmit a signal to a receiving apparatus, and the receiving apparatus processes the signal and obtains flow deformation degree and the flow deformation direction of the soil mass of the foundation layer.

Beneficial effects of the present disclosure are as follows.

The present disclosure proposes a detection apparatus for flow deformation of a foundation layer in a horizontal direction, the rotation assembly is rotatably disposed within the accommodation cavity, the measurement assembly is located within the accommodation cavity, the upper opening of the housing plugs by the top end of the rotation assembly, and therefore the rotation assembly and the measurement assembly are both protected; when the flow deformation of the soil mass of the foundation layer is tested, the flowing soil mass pushes the blade to rotate, the blade drives the rotation assembly to rotate, and the tensile strain of the first optical fiber lead wire and the tensile strain of the second optical fiber lead wire change along with rotation of the rotation assembly, and in such a way, the first optical fiber sensor measures the tensile strain of the first optical fiber lead wire and a displacement of the first optical fiber lead wire after rotation, the second optical fiber sensor measures the tensile strain of the second optical fiber lead wire and a displacement of the second optical fiber lead wire after rotation, and the flow deformation degree and the flow deformation direction of the soil mass may be determined according to a change in tensile strain before and after rotation and a change in displacement before and after rotation. The present disclosure further provides a detection method, adopting the detection apparatus for flow deformation of a foundation layer in a horizontal direction described above. When using the detection apparatus for flow deformation of a foundation layer in a horizontal direction, it does not need to consider the influence of climatic conditions, does not need to take samples, and can avoid a disturbance and a damage to a structure of the soil mass, and the detection apparatus has the potential to not only be used for evaluating the stability of the foundation in an actual engineering project, but also be used for testing the flow deformation of a soil layer in the horizontal direction in an indoor model test, which has a wide range of application.

In the drawings:
1 Housing; 2 Rotation assembly; 3 Measurement assembly; 4 Ball; 5 Elastic piece; 6 Screw; 7 Connecting rod; 8 Central hole;
11 Bottom end cover; 21 Upper end cover; 22 Blade; 23 Rotating shaft; 24 Baffle;
211 Wire hole; 311 First optical fiber sensor; 312 Second optical fiber sensor; 321 First optical fiber lead wire; 322 Second optical fiber lead wire.

DETAILED DESCRIPTION

Embodiments of the present disclosure are described in detail below, examples of the embodiments are illustrated in the drawings, and the same or similar reference numbers indicate the same or similar elements or elements having the same or similar functions throughout the drawings. The embodiments described below by reference to the drawings are exemplary and are intended for explanation of the present disclosure and are not to be construed as limiting the present disclosure.

In the description of the present disclosure, unless expressly specified or limited otherwise, the terms "coupled", "connected", and "fixed" are to be construed broadly, which, for example, may mean fixedly connected, detachably connected, or integrated; may mean mechanically connected or electrically connected; may mean directly connected, indirectly connected through an intermediate medium, or may mean inside connection of two elements or the interaction between two elements. The specific meanings of the above terms in the present disclosure may be understood according to the specific circumstances by those of ordinary skill in the art.

In the present disclosure, unless expressly specified or limited otherwise, a first feature being "on" or "under" a second feature may include the first feature and the second feature being in direct contact, or may include the first feature and the second feature not being in direct contact but being in contact with each other through additional features therebetween. Moreover, the first feature being "on", "above" and "over" the second feature includes the first feature being directly above and obliquely above the second feature, or simply represents the first feature being at a higher level than the second feature. The first feature being "under", "below" and "beneath" the second feature includes the first feature being directly below and obliquely below the second feature, or simply represents the first feature being at a lower level than the second feature.

Technical schemes of the present disclosure are described further below by way of detailed description in conjunction with the accompanying drawings.

As shown in FIGS. 1 to 4, the present embodiment provides a detection apparatus for flow deformation of a foundation layer in a horizontal direction, which includes a housing 1, a rotation assembly 2 and a measurement assembly 3. An accommodation cavity is provided inside the housing 1, and a top end of the housing 1 is provided with an upper opening communicating with the accommodation cavity. The rotation assembly 2 includes a blade 22, the rotation assembly 2 is rotatably disposed within the accommodation cavity, a top end of the rotation assembly 2 plugs the upper opening, and in response to flow deformation of a foundation layer to be monitored, a flowing soil mass is able to push the blade 22 to rotate so that the rotation assembly 2 rotates relative to the housing 1 around an axis of the rotation assembly 2. The measurement assembly 3 is disposed within the accommodation cavity and includes an optical fiber sensor and an optical fiber lead wire, the optical fiber sensor includes a first optical fiber sensor 311 and a second optical fiber sensor 312, whilst the optical fiber lead wire includes a first optical fiber lead wire 321 and a second optical fiber lead wire 322.

Figure 1:
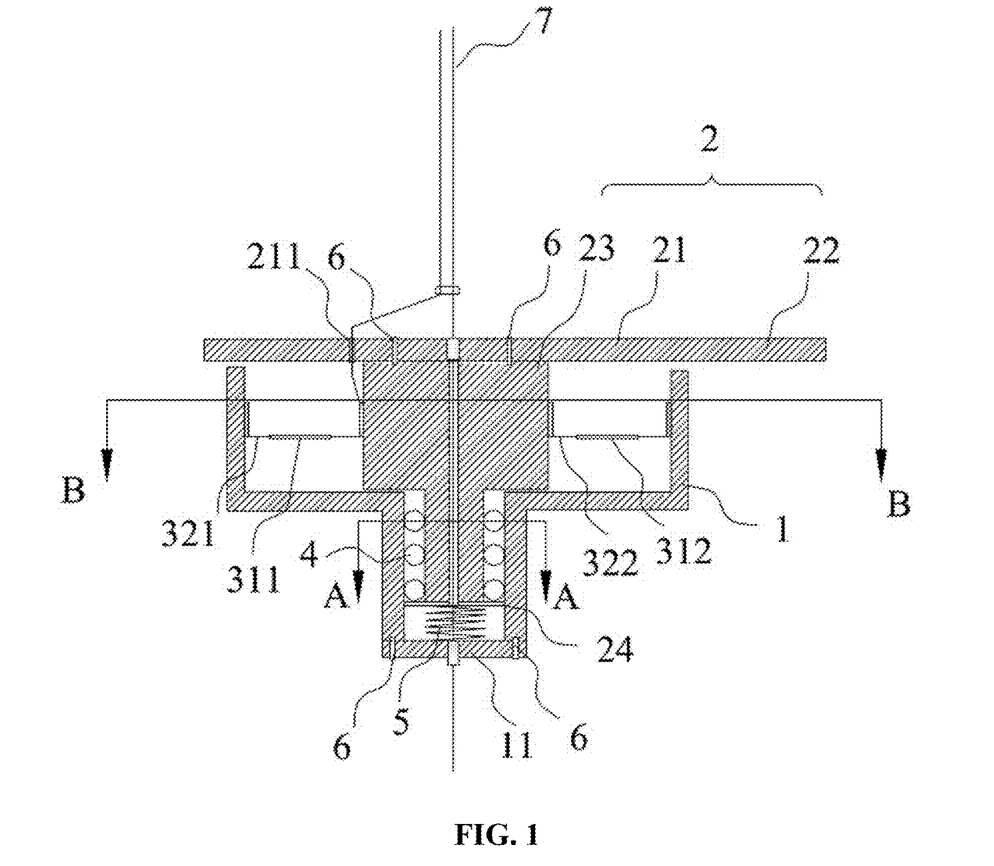
FIG. 1 is a cross-sectional view of a detection apparatus for flow deformation of a foundation layer in a horizontal direction provided in an embodiment of the present disclosure.
Figure 3:
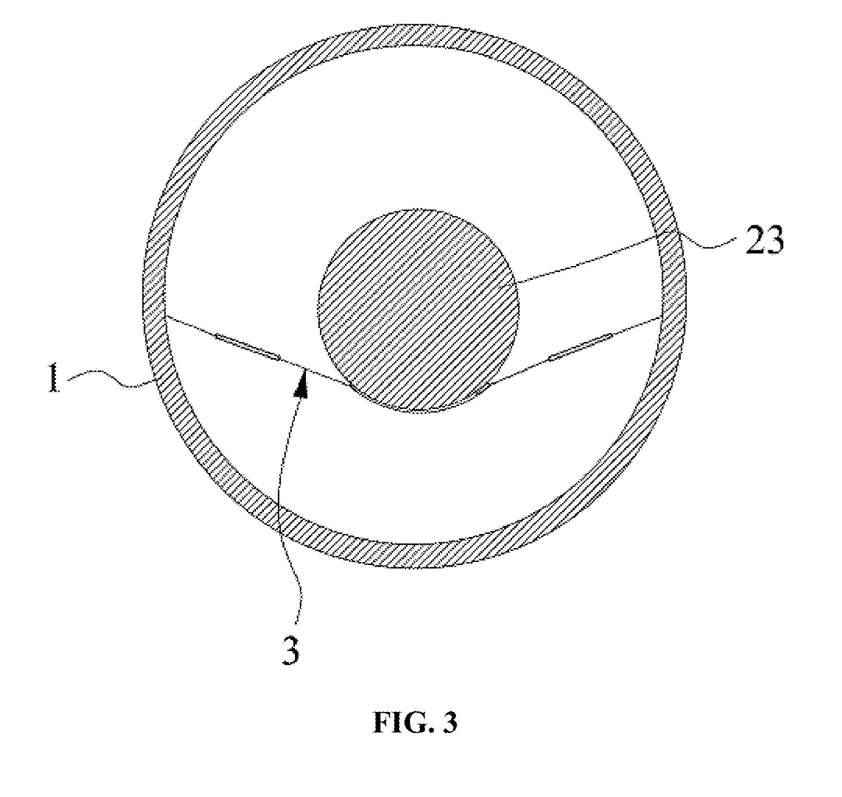
FIG. 3 is a cross-sectional view taken along B-B of FIG. 1.
Figure 4:
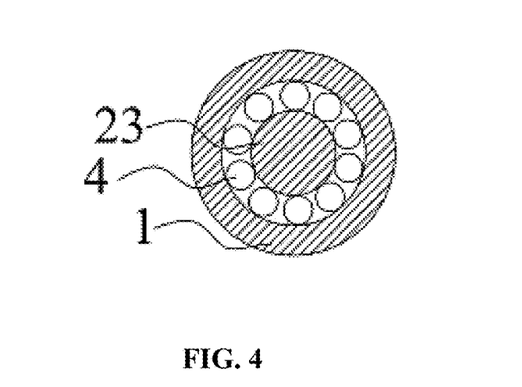
FIG. 4 is a cross-sectional view taken along A-A of FIG. 1.

The first optical fiber lead wire 321 is provided with the first optical fiber sensor 311, one end of the first optical fiber lead wire 321 is fixed to a first position point of the rotation assembly 2, the other end of the first optical fiber lead wire 321 is fixed to a second positioning point of the housing 1, and the first optical fiber sensor 311 is configured to: measure an initial value of tensile strain of the first optical fiber lead wire 321 and the first optical fiber sensor 311 before the rotation assembly 2 rotates, and measure a final value of tensile strain of the first optical fiber lead wire 321 and the first optical fiber sensor 311 after the rotation assembly 2 rotates. The second optical fiber lead wire 322 is provided with the second optical fiber sensor 312, one end of the second optical fiber lead wire 322 is fixed to a third positioning point of the rotation assembly 2, the other end of the second optical fiber lead wire 322 is fixed to a fourth position point of the housing 1, and the second optical fiber sensor 312 is configured to: measure an initial value of tensile strain of the second optical fiber lead wire 322 and the second optical fiber sensor 312 before the rotation assembly 2 rotates, and measure a final value of tensile strain of the second optical fiber lead wire 322 and the second optical fiber sensor 312 after the rotation assembly 2 rotates. The first positioning point and the third positioning point are located on a same side of the rotation assembly 2, whereas the second optical fiber lead wire 322 and the first optical fiber lead wire 321 are arranged at an obtuse angle, and the first optical fiber lead wire 321 and/or the second optical fiber lead wire 322 penetrate out of the housing 1 to be connected to a receiving apparatus. In the present embodiment, the first optical fiber lead wire 321 and the second optical fiber lead wire 322 are integrally connected, and an angle between the first optical fiber sensor 311 and the second optical fiber sensor 312 is about 120 degrees, of course, the first optical fiber lead wire 321 and the second optical fiber lead wire 322 may also be configured in two sections, and the angle between the first optical fiber sensor 311 and the second optical fiber sensor 312 is not specifically limited.

According to the detection apparatus for flow deformation of a foundation layer in a horizontal direction proposed in the present embodiment, the rotation assembly 2 is rotatably disposed within the accommodation cavity, the measurement assembly 3 is located within the accommodation cavity, the first opening of the housing 1 plugs by the top end of the rotation assembly 2, and therefore the rotation assembly 2 and the measurement assembly 3 are both protected; when a soil mass of the foundation layer is tested to flow and deform, the flowing soil mass pushes the blade 22 to rotate, the blade 22 drives the rotation assembly 2 to rotate, and the tensile strain of the first optical fiber lead wire 321 and the tensile strain of the second optical fiber lead wire 322 change along with rotation of the rotation assembly 2, and in such way, the first optical fiber sensor 311 measures the tensile strain of the first optical fiber lead wire 321 and a displacement of the first optical fiber lead wire 321 after rotation, the second optical fiber sensor 312 measures the tensile strain of the second optical fiber lead wire 322 and a displacement of the second optical fiber lead wire 322 after rotation, and the flow deformation degree and the flow deformation direction of the soil mass may be determined according to the change in tensile strain before and after rotation and the change in displacement before and after rotation.

When the detection apparatus for flow deformation of a foundation layer in the horizontal direction is used, a flow deformation of a deep soil mass may be monitored only by drilling a hole in a foundation and placing the detection apparatus in the hole. When using the detection apparatus for flow deformation of a foundation layer in the horizontal direction, it does not need to consider the influence of climatic conditions during use, does not need to take samples, and can avoid disturbance and damage to a structure of the soil mass, and the detection apparatus may not only be used for evaluating the stability of the foundation in an actual engineering project, but also be used for testing the flow deformation of a soil layer in the horizontal direction in an indoor model test, which has a wide range of application.

Figure 2:
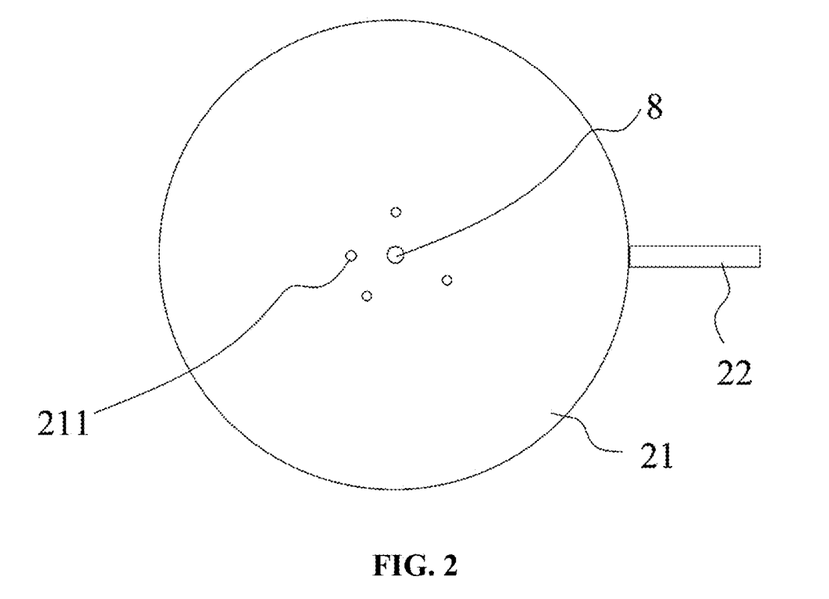
FIG. 2 is a top view of an upper end cover provided in an embodiment of the present disclosure.

Further, the rotation assembly 2 includes an upper end cover 21 and a rotating shaft 23, the upper end cover 21 is connected to the rotating shaft 23 and plugs the upper opening, and the upper end cover 21 is provided with the blade 22 in an extending radial direction. The soil mass flows to drive the blade 22 to rotate, the upper end cover 21 transmits a torque to the rotating shaft 23, and the rotating shaft 23 rotates to pull the optical fiber lead wire, so that the optical fiber lead wire is displaced and strained, and thus monitoring of flow deformation of the soil mass in the horizontal direction is converted into monitoring of movement of the rotating shaft 23. In the present embodiment, the blade 22 is integrally formed with the upper end cover 21, both the first positioning point and the third positioning point are located on the rotating shaft 23.

In some embodiments, the upper end cover 21 is connected to the rotating shaft 23 through a screw 6 so as to be convenient to disassemble, assemble and store.

Further, the upper end cover 21 is provided with a wire hole 211, and the first optical fiber lead wire 321 and/or the second optical fiber lead wire 322 penetrates through the wire hole 211 and extends out from the housing 1 after being fixed to the first positioning point on the rotating shaft 23. In the present embodiment, the second optical fiber lead wire 322 and the first optical fiber lead wire 321 are integrally connected, so that only the first optical fiber lead wire 321 needs to be penetrated out through the wire hole 211, and when the second optical fiber lead wire 322 and the first optical fiber lead wire 321 are independently and separately disposed, both the second optical fiber lead wire 322 and the first optical fiber lead wire 321 are penetrated out through the wire hole 211. The receiving apparatus in the present embodiment is an optical fiber grating demodulator, the first optical fiber lead wire 321 and/or the extended second optical fiber lead wire 322 penetrates out to connect to the optical fiber grating demodulator. The optical fiber grating demodulator is configured to emit a laser and receive a reflection spectrum, and determine a strain amount of the optical fiber sensor according to the reflection spectrum. The optical fiber grating demodulator may refer to the related art.

When the detection apparatus is assembled and the optical fiber lead wires are installed, the first optical fiber lead wire 321 and the second optical fiber lead wire 322 need to be pre-tensioned before fixing, and a process for the pre-tensioning needs to be tested through the demodulator with a pre-tensioning amount of about 8000 micro-strains. After the pre-tensioning, the optical fiber lead wire may be fixed to the rotation assembly 2 and the housing 1 through a fixing glue, where one end of the first optical fiber lead wire 321 is fixed to the housing 1 through the fixing glue, and the other end of the first optical fiber lead wire 321 is disposed to pass through the wire hole 211 and then penetrates out from the housing 1 after being fixed to the rotation assembly 2 through the fixing glue via the rotation assembly 2. In order to prevent the first optical fiver lead wire 321 from being snapped when the rotation assembly 2 rotates, a gap between the first optical fiber lead wire 321 and the wire hole 211 is plugged by the fixing glue, and thus the first optical fiber lead wire 321 is firmly fixed in the wire hole 211.

In response to the flow deformation of the soil mass, the soil mass pushes the blade 22 to rotate, the blade 22 pushes the rotation assembly 2 to rotate, the rotation assembly 2 rotates and pulls the first optical fiber lead wire 321 and the second optical fiber lead wire 322, one of the first optical fiber lead wire 321 and the second optical fiber lead wire 322 is subjected to a reduced tensile strain, and correspondingly, the other one of the first optical fiber lead wire 321 and the second optical fiber lead wire 322 is subjected to an increased tensile strain. The first optical fiber sensor 311 measures the displacement and the tensile strain of the first optical fiber lead wire 321 before rotation and the displacement and the tensile strain of the first optical fiber lead wire 321 after rotation, the second optical fiber sensor 312 measures the displacement and the tensile strain of the second optical fiber lead wire 322 before rotation and the displacement and the tensile strain of the second optical fiber lead wire 322 after rotation, the displacement change amount and the rotation direction of the rotation assembly 2 before and after rotation may be obtained, and the obtained data is deduced through a formula, which can be seen from a specifical deduction process, thereby obtaining the flow deformation degree and the flow deformation direction of the soil mass of the foundation layer in the horizontal direction. In the present embodiment, the optical fiber sensor is an optical fiber grating sensor and is connected through the optical fiber lead wire, and of course, other apparatuses such as a distributed optical fiber sensor may also be selected, which will not be repeated herein. Two optical fiber sensors are provided, so that the rotating displacement of the rotation assembly 2 may be synchronously measured, which enables high accuracy and reliable monitoring results, and avoids a problem that other results cannot be referenced and determined due to inaccurate measurements easily caused by accidents when only one optical fiber sensor is used.

Further, the rotating shaft 23 includes an upper diameter end and a lower diameter end, the accommodation cavity is divided into an upper chamber and a lower chamber being communicated with the upper chamber, the upper diameter end is accommodated in the upper chamber, and the upper diameter end and an inner wall of the upper chamber define an annular space, the measurement assembly 3 is located in the annular space, the lower diameter end is accommodated in the lower chamber, and balls 4 are filled between the lower diameter end and an inner wall of the lower chamber, and the balls 4 are used for reducing a friction mobilized between the rotating shaft 23 and the inner wall of the lower cavity. Moreover, a surface of the balls 4 may be coated with lubricating oil so as to further reduce the friction. In the present embodiment, an inner diameter of the upper chamber is larger than an inner diameter of the lower chamber, a bottom wall of the upper chamber and the inner wall of the lower chamber form a stepped surface, an outer diameter of the upper diameter end of the rotating shaft 23 is larger than an outer diameter of the lower diameter end, a bottom surface of the upper diameter end plugs an upper end opening of the lower chamber, so that the balls 4 are prevented from entering the upper chamber by mistake.

Further, a bottom of the lower diameter end is provided with a baffle 24, and the baffle 24 is used for blocking the balls 4.

In some embodiments, this apparatus further includes an elastic piece 5, and a bottom end of the rotation assembly 2 is connected to a bottom of the housing 1 through the elastic piece 5. The elastic piece 5 is used for controlling a magnitude of rotating force of the rotating shaft 23 and preventing the optical fiber lead wire from being snapped due to an excessive rotating amount of the rotating shaft 23 during an installation and implementation processes. The elastic piece 5 is preferably a spring.

In the present embodiment, a bottom end of the housing 1 is provided with a lower opening, the lower opening is communicated with the accommodation cavity, the housing 1 further includes a bottom end cover 11, and the bottom end cover 11 plugs the lower opening. The lower opening is provided, so that it is convenient for the detection apparatus to be disassembled and assembled, and for an internal condition of the housing 1 to be checked in real time.

In some embodiments, the apparatus further includes a connecting rod 7, a central hole 8 is provided on both the rotation assembly 2 and the housing 1 simultaneously along the axis of the rotation assembly 2 and the housing 1, and the connecting rod 7 is disposed to pass through the central hole 8. In the present embodiment, the connecting rod 7 is disposed to pass through the upper end cover 21, the rotating shaft 23, the interior of the spring and the bottom end cover 11 simultaneously. The connecting rod 7 is preferably a steel wire rope, and the connecting rod 7 is disposed to pass through a plurality of the detection apparatuses sequentially from top to bottom, so that soil layers at different depths may be measured.

The present embodiment further provides a detection method for flow deformation of a foundation layer in the horizontal direction. This method adopts the detection apparatus for flow deformation of a foundation layer in the horizontal direction described above and includes steps described below.

Step S0, a foundation layer is drilled, and the detection apparatus for flow deformation of a foundation layer in a horizontal direction is disposed inside the foundation layer.

Step S1, before the rotation assembly rotates, the first optical fiber sensor 311 measures an initial value of tensile strain of the first optical fiber lead wire 321 and the first optical fiber sensor 311; and the second optical fiber sensor 312 measures an initial value of tensile strain of the second optical fiber lead wire 322 and the second optical fiber sensor 312.

Step S2, a soil mass flows to push the blade 22 to rotate, and after the rotation assembly rotates, the first optical fiber sensor 311 measures a final value of tensile strain of the first optical fiber lead wire 321 and the first optical fiber sensor 311 to obtain a strain amount and a displacement change amount; and after the rotation assembly rotates, the second optical fiber sensor 312 measures a final value of tensile strain of the second optical fiber lead wire 322 and the second optical fiber sensor 312 to obtain a strain amount and a displacement change amount.

Step S3, the first optical fiber sensor (311) and the second optical fiber sensor (312) transmits a signal to a receiving apparatus, and the receiving apparatus processes the signal and obtains flow deformation degree and the flow deformation direction of the soil mass of the foundation layer.

According to the method, the rotation condition of the rotation assembly 2 may be measured according to the obtained displacement change amount and strain amount, so that the flow deformation condition of the soil mass of the foundation layer in the horizontal direction is obtained. A derivation process of theoretical relation between a flow displacement of a foundation layer in the horizontal direction and the measured result of the optical fiber sensor in the present embodiment is elaborated as follows.

Assuming that the soil mass and the blade 22 may be deformed synchronously, the soil mass is simplified into a rigid mass, the deformation of the soil mass upon encountering the blade 22 is not taken into account, and a thickness of the housing 1 is ignored.

Figure 5:
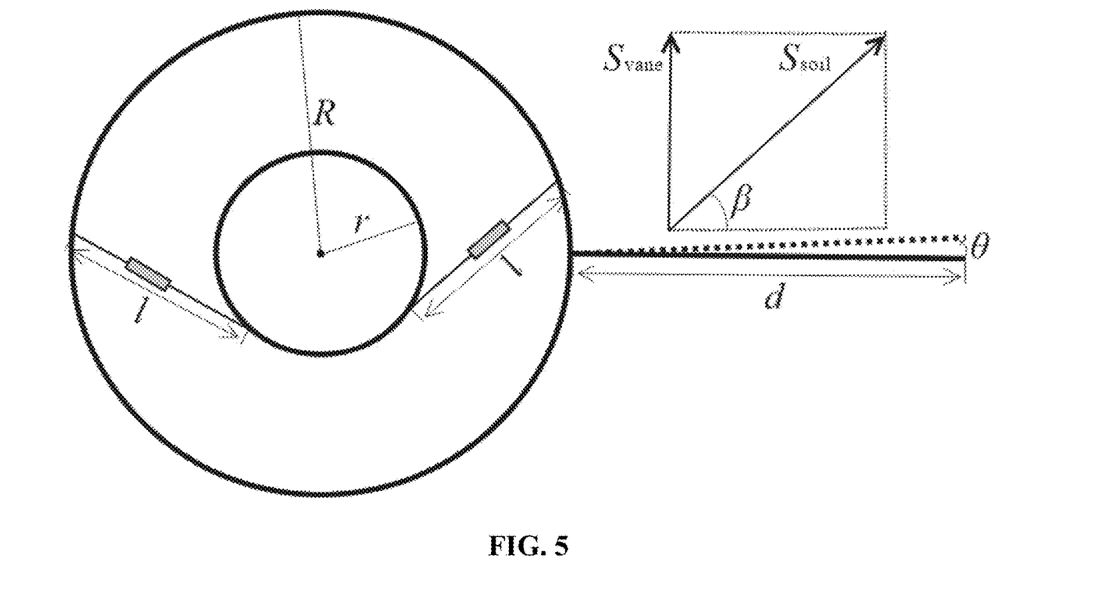
FIG. 5 is a schematic diagram of the detection method provided in an embodiment of the present disclosure.

As shown in the FIG. 5, assuming that a displacement of the deformed soil mass in the horizontal direction is $S_{soil}$ a sharp angle between the displacement of the soil mass and the blade 22 is β, a length of the blade 22 is d, a rotating angle of the blade 22 under the pushing action of the soil mass is θ, an inner diameter of the housing 1 is R, a radius of the upper diameter end of the rotating shaft 23 is r, a sum of a length of the first optical fiber sensor 311 and a length of the first optical fiber lead wire 321 (or the second optical fiber sensor 312 and the second optical fiber lead wire 322) within the accommodation cavity is l, then, according to the deformation compatibility mechanism of the soil mass and the blade 22, a rotational displacement $S_{vane}$ in a direction perpendicular to the blade 22 at a centroid position of the blade 22 may be expressed as:

$$s_{vane} = s_{soil} \sin \beta \quad (1).$$

Since the rotation measured by this apparatus is an infinitesimal deformation, in a case where θ is very small, θ may be expressed as:

$$\theta = \tan t(\theta) = \sin(\theta) = \frac{s_{soil} \sin \beta}{R + \frac{d}{2}}. \quad (2)$$

A linear displacement of rotation at the second positioning point, to which the optical fiber sensor is fixed, of the upper diameter end of the rotating shaft 23, may be expressed as:

$$s_{spindle} = \theta r = \frac{s_{soil} \sin \beta}{R + \frac{d}{2}} r. \quad (3)$$

Since the first optical fiber lead wire 321 (the second optical fiber lead wire 322) is tangent to the upper diameter end of the rotating shaft 23, a linear displacement of the second positioning point of the upper diameter end of the rotating shaft 23 is equal to the displacement change amount of the first optical fiber sensor 311 and the first optical fiber lead wire 321 (or the second optical fiber sensor 312 and the second optical fiber lead wire 322). Accordingly, the strain amount ε of both the first optical fiber sensor 311 and the first optical fiber lead wire 321 (or the second optical fiber sensor 312 and the second optical fiber lead wire 322) may be expressed as:

$$\varepsilon = \frac{s_{soil} \sin \beta}{R + \frac{d}{2}} \frac{r}{l}. \quad (4)$$

Since the optical fiber sensor is only able to measure the tensile strain, but cannot directly measure the compressive strain. In practice, the optical fiber sensor needs to be pre-tensioned firstly, and compression is derived out reversely through the amount of pre-tensioning loss. Assuming that the first optical fiber lead wire 321 and the first optical fiber sensor 311 are stretched together by a strain amount $\varepsilon_0$ during the installation process, the second optical fiber lead wire 322 and the second optical fiber sensor 312 are stretched together by a strain amount $\varepsilon_0$, and the soil mass flows to drive the first optical fiber lead wire 321 and the first optical fiber sensor 311 to be continuously stretched together, and thus the second optical fiber lead wire 322 and the second optical fiber sensor 312 are relatively compressed together, a strain value Ei of the first optical fiber sensor 311 and the first optical fiber lead wire 311 is measured in real time by an optical fiber demodulator after deformation, and the strain value Ei is expressed as:

$$\varepsilon_1 = \varepsilon_0 \frac{s_{soil} \sin \beta}{R + \frac{d}{2}} \frac{r}{l}. \quad (5)$$

A strain value $\varepsilon_2$ of the second optical fiber sensor 312 and the second optical fiber lead wire 322 is expressed as:

$$\varepsilon_2 = \varepsilon_0 \frac{s_{soil} \sin\beta}{R + \frac{d}{2}} \frac{r}{l}. \qquad (6)$$

It can be known through the formulas (5) and (6) that, although the deformation of the soil mass may be measured by only one optical fiber sensor installed within the accommodation cavity, however, the reliability and survivability are not as high as that measured and obtained by using two optical fiber sensors. Compared with the condition that one optical fiber sensor is provided, the two optical fiber sensors greatly improve the survival rate of the whole detection apparatus, and even if one of the two optical fiber sensors cannot work normally, the other optical fiber sensor may implement a detection function. Moreover, the strain amounts measured by the two optical fiber sensors are increased and decreased during the deformation process of the soil mass, and the horizontal flow direction of the soil mass may be synchronously proved. In a process of arranging the apparatus, both the orientation of the blade 22 and the position direction change of the first optical fiber sensor 311 and the second optical fiber sensor 312 are determined by rotating the connecting rod 7, and accordingly, the deformation direction of the soil mass in the horizontal direction may be determined through formulas (5) and (6). In formulas (5) and (6), other parameters except for β are known and β has the feature of randomness, so that an approximate direction of the blade 22 after rotation may be determined through the deformation of the first optical fiber sensor 311 and the second optical fiber sensor 312, but a specific direction thereof may not be determined, that is to say, a specifical value of β may not be directly obtained.

The above embodiments merely illustrate the basic principles and characteristics of the present disclosure, the present disclosure is not limited by the above embodiments, and there are various changes and modifications which fall within the claimed scope of the present disclosure without departing from the spirit and scope of the present disclosure. The claimed scope of the present disclosure is defined by the appended claims and equivalents thereof.

What is claimed is:

1. A detection apparatus for flow deformation of a foundation layer in a horizontal direction, comprising:
    a housing (1), wherein an accommodation cavity is provided inside the housing (1), and a top end of the housing (1) is provided with an upper opening communicating with the accommodation cavity;
    a rotation assembly (2), wherein the rotation assembly (2) comprises a blade (22) and is rotatably disposed within the accommodation cavity, a top end of the rotation assembly (2) plugs the upper opening, and in response to a flow deformation of a foundation layer to be monitored, a flowing soil mass is able to push the blade (22) to rotate so that the rotation assembly (2) rotates relative to the housing (1) around an axis of the rotation assembly (2); and
    a measurement assembly (3), wherein the measurement assembly (3) is disposed within the accommodation cavity, and the measurement assembly (3) comprises:
    an optical fiber sensor, wherein the optical fiber sensor comprises a first optical fiber sensor (311) and a second optical fiber sensor (312); and
    optical fiber lead wire, wherein the optical fiber lead wire comprises a first optical fiber lead wire (321) and a second optical fiber lead wire (322), wherein the first optical fiber lead wire (321) is provided with the first optical fiber sensor (311), one end of the first optical fiber lead wire (321) is fixed to a first positioning point of the rotation assembly (2), the other end of the first optical fiber lead wire (321) is fixed to a second positioning point of the housing (1), and the first optical fiber sensor (311) is configured to: measure an initial value of tensile strain of the first optical fiber lead wire (321) and the first optical fiber sensor (311) before the rotation assembly (2) rotates, and measure a final value of tensile strain of the first optical fiber lead wire (321) and the first optical fiber sensor (311) after the rotation assembly (2) rotates;
    wherein the second optical fiber lead wire (322) is provided with the second optical fiber sensor (312), one end of the second optical fiber lead wire (322) is fixed to a third positioning point of the rotation assembly (2), the other end of the second optical fiber lead wire (322) is fixed to a fourth positioning point of the housing (1), and the second optical fiber sensor (312) is configured to: measure an initial value of tensile strain of the second optical fiber lead wire (322) and the second optical fiber sensor (312) before the rotation assembly (2) rotates, and measure a final value of tensile strain of the second optical fiber lead wire (322) and the second optical fiber sensor (312) after the rotation assembly (2) rotates; and
    wherein the first positioning point and the third positioning point are located on a same side of the rotation assembly (2), the second optical fiber lead wire (322) and the first optical fiber lead wire (321) are arranged at an obtuse angle, and at least one of the first optical fiber lead wire (321) and the second optical fiber lead wire (322) penetrates out of the housing (1) to be connected to a receiving apparatus.

2. The detection apparatus for flow deformation of a foundation layer in a horizontal direction of claim 1, further comprising an elastic piece (5), and a bottom end of the rotation assembly (2) is connected to a bottom of the housing (1) through the elastic piece (5).

3. The detection apparatus for flow deformation of a foundation layer in a horizontal direction of claim 1, wherein the rotation assembly (2) further comprises an upper end cover (21) and a rotating shaft (23), the upper end cover (21) is connected to the rotating shaft (23) and plugs the upper opening, and the upper end cover (21) is provided with the blade (22) in an extending radial direction.

4. The detection apparatus for flow deformation of a foundation layer in a horizontal direction of claim 3, wherein the rotating shaft (23) comprises an upper diameter end and a lower diameter end, the accommodation cavity is divided into an upper chamber and a lower chamber being communicated with the upper chamber, the upper diameter end is accommodated in the upper chamber, and the upper diameter end and an inner wall of the upper chamber define an annular space, the measurement assembly (3) is located in the annular space, the lower diameter end is accommodated in the lower chamber, and balls (4) are filled between the lower diameter end and an inner wall of the lower chamber.

5. The detection apparatus for flow deformation of a foundation layer in a horizontal direction of claim 4, wherein a bottom of the lower diameter end is provided with a baffle (24), and the baffle (24) is configured to block the balls (4).

6. The detection apparatus for flow deformation of a foundation layer in a horizontal direction of claim 3, wherein the upper end cover (21) is provided with a wire hole (211), and at least one of the first optical fiber lead wire (321) and the second optical fiber lead wire (322) is penetrated out through the wire hole (211).

7. The detection apparatus for flow deformation of a foundation layer in a horizontal direction of claim 3, wherein the upper end cover (21) is connected to the rotating shaft (23) through a screw (6).

8. The detection apparatus for flow deformation of a foundation layer in a horizontal direction of claim 1, wherein a bottom end of the housing (1) is provided with a lower opening, the lower opening is communicated with the accommodation cavity, the housing (1) further comprises a bottom end cover (11), and the bottom end cover (11) plugs the lower opening.

9. The detection apparatus for flow deformation of a foundation layer in a horizontal direction of claim 1, further comprising a connecting rod (7), wherein a central hole (8) is provided on both the rotation assembly (2) and the housing (1) simultaneously along the axis of the rotation assembly (2) and the housing (1), and the connecting rod (7) is passed through the central hole (8).

10. A detection method for flow deformation of a foundation layer in a horizontal direction, adopting the detection apparatus for flow deformation of a foundation layer in a horizontal direction of claim 1, comprising:

Step S0, drilling a foundation layer, and disposing the detection apparatus for flow deformation of a foundation layer in a horizontal direction inside the foundation layer;

Step S1, before the rotation assembly (2) rotates, measuring, by the first optical fiber sensor (311), an initial value of tensile strain of the first optical fiber lead wire (321) and the first optical fiber sensor (311); and measuring, by the second optical fiber sensor (312), an initial value of tensile strain of the second optical fiber lead wire (322) and the second optical fiber sensor (312);

In Step S2, making a soil mass flow to push the blade (22) to rotate, and after the rotation assembly (2) rotates, measuring, by the first optical fiber sensor (311), a final value of tensile strain of the first optical fiber lead wire (321) and the first optical fiber sensor (311) to obtain a first strain amount and a first displacement change amount; and after the rotation assembly (2) rotates, measuring, by the second optical fiber sensor (312), a final value of tensile strain of the second optical fiber lead wire (322) and the second optical fiber sensor (312) to obtain a second strain amount and a second displacement change amount; and Step S3, transmitting, by the first optical fiber sensor (311) and the second optical fiber sensor (312), a signal to a receiving apparatus, processing, by the receiving apparatus, the signal, and obtaining a flow deformation degree and a flow deformation direction of the soil mass of the foundation layer.

\* \* \* \* \*